United States Patent [19]

Schmerling

[11] 3,998,895
[45] Dec. 21, 1976

[54] PREPARATION OF POLYCHLOROALKENYL AROMATIC COMPOUNDS

[75] Inventor: Louis Schmerling, Riverside, Ill.

[73] Assignee: UOP Inc., Des Plaines, Ill.

[22] Filed: Aug. 6, 1975

[21] Appl. No.: 602,498

[52] U.S. Cl. .......................................... 260/651 R
[51] Int. Cl.$^2$ ........................................... C07C 25/24
[58] Field of Search ............... 260/651 R, 653.1 R, 260/658 R, 658 C

[56] References Cited
UNITED STATES PATENTS

| 2,440,801 | 5/1948 | Hanford et al. | 260/658 C |
| 2,894,995 | 7/1959 | Schmerling | 260/651 R |
| 2,996,554 | 8/1961 | Olah et al. | 260/651 R |

Primary Examiner—D. Horwitz
Attorney, Agent, or Firm—James R. Hoatson, Jr.; Raymond E. Nelson; William H. Page, II

[57] ABSTRACT

Polychloroalkenyl aromatic compounds as exemplified by (1,3-dichloroallyl)benzene are prepared by the condensation of chloroalkyl aromatic compounds such as benzyl chloride with polychloroalkene compounds characterized by the presence of at least one chlorine atom on each of the doubly-bonded carbon atoms in the presence of a free radical-generating compound and a hydrogen chloride compound to produce the desired product.

9 Claims, No Drawings

PREPARATION OF POLYCHLOROALKENYL AROMATIC COMPOUNDS

This invention relates to a process for the preparation of polychloroalkenyl aromatic compounds. More specifically, the invention relates to a condensation of chloroalkyl aromatic compounds with polychloroalkene compounds in which at least one chloro substituent is positioned on each of the doubly-bonded carbon atoms in the presence of certain catalytic compositions of matter hereinafter set forth in greater detail. In addition, the condensation reactin is also effected in the presence of certain hydrogen chloride compounds which will act as promoters for the condensation.

The polychloroalkenyl aromatic compounds which are prepared according to the process of the present invention will find a wide variety of uses in the chemical field. For example, (1,3-dichloroallyl)benzene which is prepared by the condensation of benzyl chloride with 1,2-dichloroethylene may be hydrolyzed and dehydrochlorinated to form ketones or aldehydes such as cinnamic aldehyde which is used in flavors and in spice perfumes. Further oxidation of this aldehyde under controlled conditions will result in the preparation of cinnamic acid which is used in perfumes as well as in medicines. Another use of the (1,3-dichloroallyl)benzene would be to react this compound with hexachlorocyclopentadiene to yield a compound which possesses flame retardant properties and, thus, may be admixed with various plastics, polymers, copolymers, terpolymers, resins, polycondensates, elastomers, rubbers, textiles and fibers, both naturally occurring and synthetic in nature, coatings, paints, varnishes, leather, foams, etc., whereby the finished composition of matter will possess desirable and advantageous fire resistant or flame retardant properties. The thus prepared compositions of matter may be utilized in places which may be subjected to excessive heat or to the action of a possible flame, such places including architectural panels for construction work, wall plugs for electrical connections, soundproofing material in walls, ceilings, etc., cushions for various vehicle seats such as airplane seats, automobile seats, bus seats, truck seats, etc.

It is therefore an object of this invention to provide a process for the preparation of polychloroalkenyl aromatic compounds.

A further object of this invention is to provide a process for the condensation of chloroalkyl aromatic compounds with polychloroalkene compounds in the presence of certain catalysts to produce the desired products.

In one aspect an embodiment of this invention resides in a process for the preparation of a polychloroalkenyl aromatic compound which comprises condensing a polychloroalkene characterized by the presence of at least one chlorine atom on each of the doubly-bonded carbon atoms with a chloroalkyl aromatic compound containing at least one hydrogen atom attached to an alpha carbon atom in the presence of a hydrogen chloride compound and a catalyst comprising a free radical-generating compound at reaction conditions, and recovering the resultant polychloroalkenyl aromatic compound.

A specific embodiment of this invention is found in a process for the preparation of a polychloroalkenyl aromatic compound which comprises condensing benzyl chloride with 1,2-dichloroethylene in the presence of di-t-butyl peroxide and concentrated hydrochloric acid at a temperature in the range of from about 50° to about 300° C. and at least as high as the decomposition temperature of said free radical-generating compund, and recovering the resultant (1,3-dichloroallyl)benzene.

Other objects and embodiments will be found in the following further detailed description of the present invention.

As hereinbefore set forth the present invention is concerned with a process for the preparation of polychloroalkenyl aromatic compounds, said process involving the condensation of a chloroalkyl aromatic compound with a polychloroalkene. The condensation is effected in the presence of a catalyst comprising a free radical-generating compound and a promoter comprising a hydrogen chloride compound. Suitable chloroalkyl aromatic compounds which may be employed as one of the starting materials in the process of this invention will comprise those compounds in which at least one hydrogen atom is attached to an alpha carbon atom. In the preferred embodiment of the invention, the alkyl substituent will contain from 1 to about 4 carbon atoms and thus will include benzyl chloride, (1-chloromethyl)benzene, (2-chloroethyl)benzene, (3-chloropropyl)benzene, (4-chlorobutyl)benzene, α-(chloromethyl)naphthalene, β-(chloromethyl)naphthalene, α-(2-chloroethyl)naphthalene, β-(1-chloroethyl)naphthalene, α-(3-chloropropyl)naphthalene, β-(3-chloropropyl)naphthalene, α-(4-chlorobutyl)naphthalene, β-(2-chlorobutyl)-naphthalene, the isomeric chloromethylanthracenes, (2-chloroethyl)-anthracenes, (3-chloropropyl)anthracenes, (4-chlorobutyl)anthracenes, etc. In addition, it is also contemplated within the scope of this invention that chloroalkyl aromatic compounds may also contain an additional substituent on the aromatic ring, the only criterion being that said substituent will be relatively inert to the action of the polychloroalkenes which are employed as the other reactant in the condensation reaction. Some examples of the type of compounds which may be employed, although not necessarily with equivalent results, will include o-t-butylbenzyl chloride, m-t-butylbenzyl chloride, p-t-butylbenzyl chloride, 4-t-butyl-1-(2-chloroethyl)benzene, etc.

The second reactant which is employed in the condensation reaction of the present invention will comprise a polychloroalkenic compound characterized by the presence of at least one chlorine atom on each of the doubly-bonded carbon atoms. Thus, some specific examples of the compounds which may be used will include 1,2-dichloroethylene, 1,1,2-trichloroethylene, tetrachloroethylene, 1,2-dichloropropene-1, 1,1,2-trichloropropene-1, 1,2-dichlorobutene-1, 1,1,2-trichlorobutene-1, 2,3-dichlorobutene-2, 1,2,3-trichlorobutene-2, 1,1,2,3-tetrachlorobutene-2, 1,2,3,4-tetrachlorobutene-2, etc. It is to be understood that the aforementioned polychloroalkenic compounds which contain from 2 to about 4 carbon atoms are only representative of the class of compounds which may be used, and that the present invention is not necessarily limited thereto.

The condensation of the chloroalkyl aromatic compound and the polychloroalkenic compound is effected in the presence of certain catalytic compositions of matter, said catalysts comprising a compound which will generate free radicals at the conditions of temperature and pressure under which the present reaction takes place. Examples of these catalysts will include in particular organic peroxy compounds containing the bivalent radical —O—O— which is capable of inducing the condensation reaction. The organic compounds which constitute a preferred class of catalysts for use in this invention will include peracetic acid, persuccinic acid, dimethyl peroxide, diethyl peroxide, dipropyl peroxide, di-t-butyl peroxide, butyryl peroxide, lauroyl peroxide, benzoyl peroxide, tetrahydronaphthalene peroxide, urea peroxide, t-butyl perbenzoate, t-butyl hydroperoxide, methylcyclohexyl hydroperoxide, cyclohexanone peroxide, cumene hydroperoxide, etc. It is also contemplated within the scope of this invention that organic peroxy compounds which are compounded commercially with various diluents for use as free radical-generating agents may be used and will include benzoyl peroxide compounded with calcium sulfate, benzoyl peroxide compounded with camphor, etc. Only catalytic amounts (less than stoichiometric amounts) are needed.

The reaction of the present process involving the aforementioned starting materials is effected at elevated reaction temperatures which should be at least as high as the initial decomposition temperature of the free radical-generating catalyst, such as the peroxide compound, in order to liberate and form free radicals which promote the reaction. In selecting a particular reaction temperature for use in the process of the present invention, two considerations must be taken into account. First sufficient energy by means of heat must be supplied to the reaction system so that the reactants, namely, the chloroalkyl aromatic compound and the polychloroalkenic compound will be activated sufficiently for radical transfer to take place when free radicals are generated by the catalyst. Second, free radical-generating catalysts such as peroxy compounds, particularly organic peroxides, decompose at a measurable rate with time in a logarithmic function dependent upon temperature. This rate of decomposition can be and ordinarily is expressed as the half life of a peroxide at a particular temperature. For example, the half life in hours for di-t-butyl peroxide is 17.5 hours at 125° C., 5.3 hours at 135° C. and 1.7 hours at 145° C. (calculated from data for the first 33% decomposition). A reaction system temperature must then be selected so that the free radical-generating catalyst decomposes smoothly with the generation of free radicals at a half life which is not too long. In other words, sufficent free radicals must be present to induce the present chain reaction to take place, and these radicals must be formed at a temperature at which the reactants are in a suitably activated state for conversion. When the half life of the free radical-generating catalyst is greater than 10 hours, radicals are not generated at a sufficient rate to cause the reaction to go forward at a sufficiently detectable rate. Thus, the reaction temperature may be within the range of from about 50° to about 300° C. and at least as high as the decomposition temperature of the catalyst, by which is meant a temperature such that the half life of the free radical-generating catalyst is not greater than 10 hours. Since the half life for each free radical-generating catalyst is different at different temperatures, the exact temperature to be utilized in a particular reaction will vary. However, persons skilled in the art are well acquainted with the half life vs. temperature data for different free radical-generating catalysts and thus, it is within the skill of one familiar with the art to select the particular temperature needed for any particular catalyst. However, the operating temperatures generally do not exceed the decomposition temperature of the catalyst by more than about 150° C. For example, when a free radical-generating catalyst such as t-butyl perbenzoate is used having a decomposition temperature of approximately 115° C., the operating temperature of the process is from about 115° C. to about 265° C. When di-t-butyl peroxide having a decomposition temperature of about 130° C. is used, the process is run at a temperature ranging from about 130° to about 280° C. Higher reaction temperatures may be employed, but little is gained if the temperature is more than the hereinbefore mentioned 150° C. higher than said decomposition temperature of the catalyst.

In addition to the elevated temperatures which are utilized, the reaction may also be effected at elevated pressures ranging from about 1 to about 100 atmospheres or more, the preferred operating pressure of the process being that which is required to maintain a substantial portion of the reactants in liquid phase. Pressure is not an important variable in the process of this invention. However, because of the low boiling points of some of the reactants, it is necessary to utilize pressure-withstanding equipment to insure liquid phase conditions. In batch type operations, it is often desirable to utilize pressure-withstanding equipment, to charge the reactants and the catalyst to the vessel, and to pressure the vessel with 10, 30, 50 or more atmospheres with an inert gas such as nitrogen. This helps to insure the presence of liquid phase conditions. However, when the molar quantity of reactants is sufficient, the pressure which they themselves generate at the temperature utilized is sufficient to maintain the desired phase conditions.

Although the above discussion concerns the use of a compound containing a bivalent —O—O— radical, it is also contemplated within the scope of this invention that other free radical-generators may also be used to initiate the condensation reaction. Some specific examples of these other free radical-generators will include organometallic compounds such as tetramethyllead, tetraethyllead, tetrapropyllead, etc., ultra-violet light, etc., azobis-(isobutyronitrile), etc., In addition to effecting the condensation of the chloroalkyl aromatic compound and the polychloroalkenic compound in the presence of a catalyst of the type hereinbefore set forth, the reaction is also effected in the presence of a promoter which comprises a hydrogen chloride compound. The aforementioned hydrogen chlorie compound may be in an anhydrous or aqueous state. For example, when an aqueous hydrogen chloride compound is used, it may comprise hydrochloric acid in various concentrations, a preferred acid which is used in the process of this invention constituting concentrated hydrochloric acid which has a 38% concentration. The aforementioned hydrogen chloride compound is usually present in the reaction mixture in a quantity range from about 1 to about 20 weight percent of hydrogen chloride to the organic peroxy compound which is used as the catalyst.

The process of this invention may be effected in any suitable manner and may comprise either a batch or continuous type operation. For example, when a batch type operation is used, a quantity of the chloralkyl aromatic compound characterized by the presence of at least one hydrogen atom attached to an alpha carbon atom and the polychloroalkenic compound characterized by the presence of at least one chlorine atom on each of the doubly-bonded carbon atoms are placed in an appropriate apparatus along with the free radical-generating compound which acts as a catalyst and the hydrogen chloride compound. A particularly suitable type of reaction apparatus for the condensation reaction comprises an autoclave of the rotating or mixing type. The liner is sealed into the autoclave and, if superatmospheric pressures are desired, an inert gas such as nitrogen is pressed in until the desired operating pressure is reached. Thereafter, the apparatus and contents thereof are then heated to the desired operating temperature which is at least as high as the decomposition temperature of the free radical-generating compound and preferably not greater than about 150° C. higher than the decomposition temperature. After maintaining the apparatus and contents thereof at the desired operating conditions of temperature and pressure for a predetermined residence time, which may range from about 0.5 up to about 10 hours or more in duration, heating of the apparatus is discontinued and the vessel and contents thereof are then allowed to cool to room temperature. After reaching room temperature, the excess pressure is discharged, the apparatus is opened, and the reaction mixture is recovered therefrom. The reaction mixture may then be subjected to conventional means of separation and purification, said means including but not limited to, filtration, extraction, washing, drying, distillation, etc., whereby the desired product comprising the polychloroalkenyl aromatic compound is separated and recovered from any starting materials which still may be present.

It is also contemplated within the scope of this invention that the condensation reaction may be effected in a continuous manner of operation. When such a type of operation is used, the starting materials comprising the chloroalkyl aromatic compound and the polychloroalkenic compound are continuously charged to a reaction zone which is maintainted at the proper operating conditions of temperature and pressure. In addition, the particular free radical-generating compound which acts as a catalyst for the reaction and the hydrogen chloride compound are also continuously charged thereto. The two reactants and the catalyst and promoter may be charged to the reactor through separate lines or, if so desired, the catalyst may be admixed with one or both of the reactants prior to entry into said reactor and the mixture then charged thereto in a single stream. Upon completion of the desired residence time, the reactor effluent is continuously withdrawn and subjected to conventional means of separation of a type similar to those hereinbefore set forth whereby the desired product comprising a polychloroalkenyl aromatic compound may be recovered, while any unreacted starting materials will be recycled to the reaction zone to form a portion of the feed stock.

Some representative examples of the type of polychloroalkenyl aromatic compounds which may be prepared by the condensation reaction of this invention will include (1, 3-dichloroallyl)benzene, (1, 3-dichloro-1-methylallyl)benzene, (1-chloromethyl-3-chloroallyl)benzene, (1, 3-dichlorocrotyl)benzene, (1,3-dichloro-1-ethylallyl)benzene, (1, 3, 3-trichloroallyl)benzene, (1, 3, 3-trichlorocrotyl)benzene, (1, 3, 4-trichlorocrotyl)benzene, 1-(1, 3-dichloroallyl)naphthalene, 2-(1, 3-dichloroallyl)naphthalene, 2-(1, 3, 3-trichloroallyl)naphthalene, 9-(1, 3-dichloroallyl)anthracene, 9-(1, 3-dichlorocrotyl)anthracene, etc. It is to be understood that the aforementioned polychloroalkenyl aromatic compounds are only representative of the class of compounds which may be prepared, and that the present invention is not necessarily limited thereto.

The following examples are given for purposes of illustrating the process of the present invention. However, these examples are not intended to limit the generally broad scope of the present invention in strict accordance therewith.

EXAMPLE I

To the glass liner of a rotating autoclave is charged 126.5 grams (1.0 mole) of benzyl chloride and 97 grams (1.0 mole) of 1, 2-dichloroethylene. In addition, 18 grams of concentrated hydrochloric acid (38% concentration) and 17 grams of water along with 6 grams of di-t-butyl peroxide are also placed in the autoclave. The glass liner is then sealed into the autoclave and nitrogen is pressed in until an initial operating pressure of 30 atmospheres is reached. Following this, the autoclave is then heated to a temperature of 130° C. and maintained in a range of from 130° –140° C. for a period of 8 hours. At the end of the 8-hour period, heating is discontinued and the autoclave is allowed to return to room temperature. Upon reaching room temperature the excess pressure is discharged, the autoclave is opened and the reaction product is recovered therefrom. The two layers are separated; the upper organic layer is washed with water, dried and subjected to fractional distillation. The desired product comprising (1, 3-dichloroallyl)benzene is recovered from this fractional distillation.

EXAMPLE II

In a manner similar to that set forth in Example I above 126.5 grams (1.0 mole) of benzyl chloride and 111 grams (1.0 mole) of 1, 2-dichloropropene-1 are placed in the glass liner of a rotating autoclave along with 6 grams of di-t-butyl peroxide and 17 grams of concentrated hydrochloric acid. After sealing the glass liner into the autoclave and pressuring with nitrogen until an initial operating pressure of 30 atmospheres is reached, the autoclave is then heated to a temperature of 130° C. and maintained in a range of from 130° –140° C. for a period of 6 hours. At the end of this time, heating is discontinued, the autoclave is allowed to return to room temperature and the excess pressure is vented therefrom. After opening the autoclave, the reaction mixture is recovered, washed, dried and subjected to fractional distillation whereby the desired product comprising (1, 3-dichlorocrotyl)benzene is separated and recovered.

EXAMPLE III

In this example 70 grams (0.5 mole) of (2-chloroethyl)benzene and 66 grams (0.5 mole) of trichloroethylene along with 25 grams of concentrated hydrochloric acid and 6 grams of benzoyl peroxide are placed in the glass liner of a rotating autoclave. The liner is sealed into the autoclave and nitrogen pressed in until an initial operating pressure of 30 atmospheres is reached. The autoclave is then heated to a temperature of 80° C. and maintained in a range of from 80° –90° C. for a period of 6 hours. At the end of this 6-hour period, heating is discontinued, the autoclave is allowed to return to room temperature and the excess pressure is discharged therefrom. The autoclave is opened, the reaction mixture is recovered and the upper organic layer is separated from the lower aqueous layer. After fractionation of the upper layer the presence of the desired compound comprising (1-chloromethyl-3, 3-dichloroallyl)benzene is confirmed by preparative gas chromatography followed by infrared analysis.

EXAMPLE IV

To a reaction flask provided with heating, stirring and refluxing means is charged 88 grams (0.5 mole) of α-chloromethylnaphthalene and 48.5 grams (0.5 mole) of dichloroethylene along with 25 grams of concentrated hydrochloric acid and 6 grams of di-t-butyl peroxide. The flask and contents thereof are heated to a temperature of 130° C. and maintained in a range of from 130°–140° C. for a period of 8 hours. At the end of this time, heating is discontinued and after the reaction mixture is allowed to return to room temperature the upper layer is separated from the lower aqueous layer. The upper layer is then washed, dried, and subjected to fractional distillation, the bottoms from said distillation being submitted to preparative gas chromatography followed by infrared analysis. These analyses will disclose the presence of the desired compound which is α-(1, 3-dichloroallyl)naphthalene.

EXAMPLE V

To the glass liner of a rotating autoclave is added 63 grams (0.5 mole) of benzyl chloride, 65.7 grams (0.5 mole) of trichloroethylene, 6 grams of benzoyl peroxide, 20 grams of concentrated hydrochloric acid (38% concentration) and 15 grams of water. The liner is sealed into the autoclave and pressured with 30 atmospheres of nitrogen. Upon reaching the desired operating pressure, the autoclave is then heated to a temperature of 80° C. and maintained in a range of from 80° –90° C. for a period of 8 hours. At the end of the 8-hour period, heating is discontinued, the autoclave is allowed to return to room temperature and the excess pressure is discharged therefrom. After opening the autoclave and recovering the reaction mixture, the organic layer is separated from the aqueous layer, washed with water and subjected to fractional distillation. The bottoms recovered from the distillation are submitted to preparative gas chromatography followed by infrared analysis. These analyses will disclose the presence of the desired product comprising (1, 3, 3-trichloroallyl)benzene.

I claim as my invention:

1. A process for the preparation of a polychloroalkenyl aromatic compound which comprises condensing a polychloroalkene containing from 2 to about 4 carbon atoms and characterized by the presence of at least 1 chlorine atom on each of the doubly-bonded carbon atoms with a chloroalkyl aromatic compound containing at least 1 hydrogen atom attached to an alpha carbon atom in the presence of hydrogen chloride and a catalyst comprising a free radical-generating compound at a temperature in the range of from about 50° to about 300° C. and at least as high as the decomposition temperature of said free radical-generating compound, and recovering the resultant polychloroalkenyl aromatic compound.

2. The process as set forth in claim 1 in which said free radical-generating compound is an organic peroxy compound.

3. The process as set forth in claim 2 in which said organic peroxy compound is di-t-butyl peroxide.

4. The process as set forth in claim 1 in which said hydrogen chloride is in the form of concentrated hydrochloric acid.

5. The process as set forth in claim 1 in which said chloroalkyl aromatic compound is benzyl chloride, said polychloroalkene is 1, 2-dichloroethylene and said polychloroalkenyl aromatic compound is (1, 3-dichloroallyl)benzene.

6. The process as set forth in claim 1 in which said chloroalkyl aromatic compound is benzyl chloride, said polychloroalkene is 1, 2-dichloropropene-1, and said polychloroalkenyl aromatic compound is (1, 3-dichlorocrotyl)benzene.

7. The process as set forth in claim 1 in which said chloroalkyl aromatic compound is (2-chloroethyl)benzene, said polychloroalkene is trichloroethylene, and said polychloroalkenyl aromatic compound is (1-chloromethyl-3, 3-dichloroallyl)benzene.

8. The process as set forth in claim 1 in which said chloroalkyl aromatic compound is α-chloromethylnaphthalene, said polychloroalkene is 1, 2-dichloroethylene, and said polychloroalkenyl aromatic compound is α-(1, 3-dichloroallyl)naphthalene.

9. The process as set forth in claim 1 in which said chloroalkyl aromatic compound is benzyl chloride, said polychloroalkene is trichloroethylene, and said polychloroalkenyl aromatic compound is (1, 3,-3-trichloroallyl)benzene.

* * * * *